United States Patent
Holland et al.

(10) Patent No.: US 10,730,756 B2
(45) Date of Patent: Aug. 4, 2020

(54) COLLOIDAL COMPOSITIONS AND METHODS OF PREPARING SAME

(71) Applicant: Ecolab USA Inc., St. Paul, MN (US)

(72) Inventors: Brian T. Holland, Oak Park, IL (US); Francois Batllo, Burr Ridge, IL (US); Carmen Y. Ortiz, Woodridge, IL (US); Dennis L. MacDonald, Wheaton, IL (US)

(73) Assignee: ECOLAB USA INC., St. Paul, MN (US)

( * ) Notice: Subject to any disclaimer, the term of this patent is extended or adjusted under 35 U.S.C. 154(b) by 290 days.

(21) Appl. No.: 15/877,168

(22) Filed: Jan. 22, 2018

(65) Prior Publication Data

US 2018/0141822 A1    May 24, 2018

Related U.S. Application Data

(63) Continuation of application No. 10/827,214, filed on Apr. 19, 2004, now abandoned.

(51) Int. Cl.

| | |
|---|---|
| *C01B 33/20* | (2006.01) |
| *B01J 13/00* | (2006.01) |
| *B82Y 30/00* | (2011.01) |
| *C01B 33/141* | (2006.01) |
| *C01B 33/26* | (2006.01) |
| *C01B 37/02* | (2006.01) |
| *C01B 39/02* | (2006.01) |
| *A61K 8/25* | (2006.01) |
| *A61K 8/41* | (2006.01) |
| *A61Q 19/00* | (2006.01) |
| *A61K 8/04* | (2006.01) |
| *A61K 8/19* | (2006.01) |

(52) U.S. Cl.
CPC .............. *C01B 33/20* (2013.01); *A61K 8/042* (2013.01); *A61K 8/19* (2013.01); *A61K 8/25* (2013.01); *A61K 8/416* (2013.01); *A61Q 19/00* (2013.01); *B01J 13/0008* (2013.01); *B82Y 30/00* (2013.01); *C01B 33/141* (2013.01); *C01B 33/26* (2013.01); *C01B 37/02* (2013.01); *C01B 39/02* (2013.01); *A61K 2800/10* (2013.01); *C01P 2004/62* (2013.01); *C01P 2004/64* (2013.01); *C01P 2006/12* (2013.01)

(58) Field of Classification Search
CPC . A61K 8/042; A61K 8/19; A61K 8/25; A61K 8/416; A61K 2800/10; A61Q 19/00; B01J 13/0008; B82Y 30/00; C01B 33/141; C01B 33/20; C01B 33/26; C01B 33/02; C01B 39/02; C01P 2004/62; C01P 2004/64; C01P 2004/12
See application file for complete search history.

(56) References Cited

U.S. PATENT DOCUMENTS

| | | | |
|---|---|---|---|
| 1,552,341 A | 9/1925 | Poetschke | |
| 2,736,668 A | 2/1956 | Broge | |
| 2,913,419 A | 11/1959 | Alexander | |
| 2,974,108 A * | 3/1961 | Alexander | ........... B01J 13/0013 516/79 |
| 3,442,795 A | 5/1969 | Kerr et al. | |
| 4,287,086 A | 9/1981 | Finlayson et al. | |
| 4,410,501 A * | 10/1983 | Taramasso | ............... B01J 29/89 423/705 |
| 4,666,692 A | 5/1987 | Taramasso et al. | |
| 4,670,617 A | 6/1987 | DeSimone | |
| 5,024,826 A | 6/1991 | Linton | |
| 5,221,497 A * | 6/1993 | Watanabe | ............. C01B 33/145 106/287.34 |
| 5,358,882 A | 10/1994 | Bertagnolli et al. | |
| 5,558,851 A | 9/1996 | Miller | |
| 5,597,512 A | 1/1997 | Watanabe et al. | |
| 6,191,323 B1 | 2/2001 | Nemeth et al. | |
| 6,306,364 B1 * | 10/2001 | Valencia | ............... C01B 39/085 423/326 |
| 6,358,882 B1 | 3/2002 | Salem et al. | |
| 6,669,924 B1 | 12/2003 | Kaliaguine et al. | |
| 2005/0014000 A1 | 10/2005 | Bringley et al. | |
| 2007/0034116 A1 | 2/2007 | MacDonald | |
| 2007/0104643 A1 | 5/2007 | Holland | |
| 2009/0018219 A1 | 1/2009 | MacDonald | |
| 2010/0104500 A1 | 4/2010 | Holland | |

FOREIGN PATENT DOCUMENTS

| | | |
|---|---|---|
| CN | 1036547 A | 10/1989 |
| EP | 0109060 | 5/1984 |
| EP | 0335195 | 10/1989 |
| WO | WO 94/13584 A1 | 6/1994 |

OTHER PUBLICATIONS

Heinrichs, B. et al. "Palladium-Silver Sol-Gel Catalysts for Selective HydrodechlLorination of 1, 2-Dichloroethane into Ethylene", Journal of catalysis, Vo. 172, 1997, pp. 322-335.

Heinrichs, B. et al., Pd/SiO$_2$ Cogelled Aerogel Catalysts and Impregnated Aerogel and Xerogel Catalysts: Synthesis and Characterization, Journal of Catalysis, vol. 170, 1997, pp. 366-376.

Breitscheidel, B. et al. "Metal Complexes in Inorganic Matrices. Nanometer-Sized, Uniform Metal Particles in a SiO$^2$, Matrix by Sol-Gel Processing of Metal Complexes." Chemistry of Materials, vol. 3, 1991, pp. 559-566.

Hermans, L.A.M.; Geus, J.W., Interaction of nickel ions with silica supports during deposition-precipitation, Studies in Surface Science and Catalysis, 1979, 3, 113-130.

(Continued)

*Primary Examiner* — Christopher M Rodd

(74) *Attorney, Agent, or Firm* — Eric D. Babych; Barnes & Thornburg LLP

(57) ABSTRACT

Colloidal compositions and methods of preparing same are provided. The colloidal compositions include a silicate and a metal dispersed therein. The colloidal compositions can further include a stabilizer, such as a quaternary amine, to enhance the and dispersion of the metal loading within the silicate. The colloidal compositions can be made such that the metal is dispersed within the silicate in a controlled manner.

9 Claims, No Drawings

(56) References Cited

OTHER PUBLICATIONS

Lambert, S et al., "Synthesis of Pd/SiO$_2$, Ag/SiO$_2$, and Cu/SiO$_2$ cogelled xerogel catalysts: study of metal dispersion and catalytic activity," Journal of Catalysis, vol. 221, 2004, pp. 335-346.

Lopez, T. et al, "Pt/SiO$_2$ Sol-Gel Catalysts: Effects of pH and Platinum Precursor," Journal of Physical Chemistry, vol. 97, 1993, pp. 1671-1677.

Mizukoshi, Y. et al., "Sonochemical Preparation of Bimetallic Nanoparticles of Gold/Palladium in Aqueous Solutions," Journal of Physical Chemistry B, vol. 101, No. 36, 1997, pp. 7033-7097.

Mörke, W. et al., "Metal Complexes in Inorganic Matrices. Composition of Highly dispersed Bimetallic Ni, Pd Alloy Particles Prepared by Sol-Gel Processing: Electron Microscopy and Ferromagnetic Resonance Study," Chemistry of Materials, vol. 6, 1994, pp. 1659-1666.

Tanaka, S. et al., "Preparation of highly dispersed silica-supported palladium catalysts by a complexing agent-assisted sol-gel method and their characteristics," Applied Catalysis A: General, vol. 229, 2002, pp. 165-174.

Ueno, A. et al. "Particle-size Distribution of Nickel Dispersed on Silica and its Effects on Hydrogenation of Propionaldehyde," Journal of Chemical Society, Faraday Translation 1, vol. 79, 1983, pp. 127-136.

Holland et al., "Dual Templating of Macroporous Silicates with Zeolitic Microporous Frameworks," J.Am. Chem. Soc. 1999, 121, 4308-4309.

The Merriam-Webster Unabridged Dictionary., Online@http://www.merriam-webster.com/dictionary/lattice (copyright 2014), Headword: lattice, layer; p. 1 of 1.

Lewis, Richard J., Sr. (2002) Hawley's Condensed Chemical Dictionary (14$^{th}$ Edition), John Wiley & Sons, Online@http://knovel.com/web/portal/browse/dsplay?_EXT_KNOVEL_DISPLAY_bookid=704&VerticalID=O, headword="amorphous", "dislocation", "impurity", and "lattice", (Knovel Release Date: Sep 4, 2003; downloaded May 25, 2010), pp. 1-2.

A. Tuel, "Crystallization of titanium silicalite-1 from gels containing hexanediamine and tetrapropylammonlum bromide", Original Research Article Progress in Zeolite and Microporous Materials, Studies in Surface Science and Catalysis, (Chon, et al. Editors), vol. 105, 1997, pp. 261-268, online@http://www.sciencedirect.com/.

The Merck Index An Encyclopedia of Chemicals, Drugs and Biologicals, Tenth Edition, (Merck & Co, Inc. Rahway, NJ, 1983) pp. 149 & 667, Jan. 17, 1984.

S. Mintova et al, "Effect of the silica source on the formation of nanosized silicalite-1: an in situ dynamic light scattering study", Microporous and Mesoporous Materials, 55 (2002), pp. 171-179, from online@www.elsevier.com/locate/micromeso.

Cundy et al, "Some observations on the preparations and properties of colloidal silicalites. Part I: Synthesis of colloidal silicalite-1 and titanosilicalite-1 (TS-1)", Microporous and Mesoporous Materials, 66 (2003), pp. 143-156, from online@www.sciencedirect.com.

* cited by examiner

COLLOIDAL COMPOSITIONS AND METHODS OF PREPARING SAME

SUMMARY OF THE INVENTION

The present invention generally relates to colloidal compositions and methods of producing same. In particular, the present invention relates to colloidal compositions that include a silicate with a metal dispersed within the silicate and at varying metal loadings that can range from as high as about 35 wt % based on silica. The colloidal compositions can further include a stabilizer, such as a quaternary compound, that can facilitate the dispersion and loading of the metal within the silicate.

In this regard, the present invention provides a novel and unique alternative to conventional surface-treated silica colloids. The colloidal compositions of the present invention can be made in any suitable way. Preferably, the colloidal compositions are, in general, synthesized according to two procedures as further detailed below pursuant to various embodiments of the present invention.

According to the first synthesis procedure, a method of producing a silica colloid includes providing an alkaline solution having a stabilizing component, adding a silicic acid solution to the alkaline solution, and forming a colloid of silica particles wherein the stabilizing component is dispersed throughout each particle. Further, a cationic metal component can be added to the stabilizer-containing alkaline solution in an embodiment. Addition of the silicic acid solution to the alkaline solution thus forms a colloid of silica particles having both the stabilizing component and the metal component dispersed within one or more of the silicate particles, such as in a homogenous manner.

In an embodiment, the stabilizer is a quaternary compound, preferably a quaternary amine, such as a quaternary ammonium hydroxide and the like. The stabilizer performs several functions in the synthesis of the colloidal silica. For example, the stabilizer provides the OH⁻ component to the alkaline solution, which catalyzes the reaction between the silicic acid and metal component to form the colloid. The stabilizer also enables more of the metal component to bond or chemically combine with the silica component during formation of the colloid. The resultant silica colloid demonstrates the capability to carry increased amounts of metal. The colloid can have a metal content from about 0.0001 wt % to about 35 wt % based on silica. The colloidal particles are amorphous and spherical in shape. In addition, the colloidal composition can be further processed to produce a crystalline structure as described in greater detail below. The diameter of the colloidal particles is in the range of about 2 nm to about 1000 nm according to an embodiment.

According to the second synthesis procedure, a method of preparing a metal-containing silica colloid is provided wherein a silicic acid solution is reacted with a cationic metal component to form a metal silicate solution. The metal silicate solution is subsequently added to an alkaline solution to form a colloid of metal silicate particles. Reacting the silicic acid solution with the metal component forms a metal-silicate monomer that is subsequently polymerized as the metal silicate solution is added to the alkaline solution. The polymerization forms a homogeneous metal-silicate lattice microstructure or framework throughout the entire solid phase of the colloid.

The polymerization of the metal-silicate and the utilization of a polyvalent cationic metal component in formation of the colloid yields a metal silicate colloids having metal content in the range of about 0.0001% to as high as 2% by weight silica according to an embodiment. The lattice metal-silicate structure throughout the entire solid phase also improves the stability of the colloid. The metal silicate colloid of the present invention remains soluble throughout the entire pH range, i.e., pH 1-14. The solid phase of the metal silicate colloid of the present invention is substantially amorphous having a generally spherical particle shape and size in the range of from about 2 nm to about 1000 nm according to an embodiment.

With the second synthesis procedure, the location of a metal component within the metal-containing silica colloid can be effectively controlled. The metal silicate solution and the silicic acid solution can be selectively added to the alkaline solution to form a colloid of silica particles containing metal that is dispersed within one or more of the particles. The sequence and duration in which the metal silicate solution and the silicic acid solution are added effectively controls the location of the metal within the solid phase of the colloid. For example, the metal silicate solution can be added to the alkaline solution before the silicic acid solution to form a colloid of silica particles having metal dispersed within an interior core layer of each particle. Alternatively, the silicic acid solution can be added to the alkaline solution before the metal silicate solution to form a colloid of silica particles having a silica core and metal dispersed within an outer or exterior layer of each particle. Moreover, the metal silicate solution and the silicic acid solution can be added to the alkaline solution in an alternating manner to form a colloid of silica particles having a number of layers, wherein the layers alternate between metal containing layers and layers containing only silica in a repeat or successive manner.

To this end, in an embodiment, the present invention provides a colloidal composition. The colloidal composition includes a silicate doped with a metal, and a stabilizer dispersed within the silicate.

In an embodiment, the silicate doped with metal includes about 35 wt % or less of metal based on silica.

In an embodiment, the stabilizer includes a quaternary compound.

In an embodiment, the quaternary compound is a quaternary amine.

In an embodiment, an amount of the stabilizer correlates to an amount of the metal.

In another embodiment, the present invention provides a colloidal silicate composition doped with a metal. The colloidal silicate composition includes one or more silicate particles wherein the metal is dispersed within one or more of the silicate particles.

In an embodiment, the metal is dispersed in a controlled manner.

In an embodiment, one or more of the silicate particles includes a layered structure.

In an embodiment, the metal is controllably dispersed within one or more particle layers of the layered structure.

In an embodiment, the metal includes an alkali metal, an alkaline earth metal, a $1^{st}$ row transition metal, a $2^{nd}$ row transition metal, a lanthanide, and combinations thereof.

In an embodiment, the metal is about 2 wt % or less based on silica.

In yet another embodiment, the present invention provides a method of forming a colloidal composition. The method includes preparing a heel solution including a stabilizer; preparing a silicic acid solution; and mixing and further processing the heel solution and the silicic acid solution to form the colloidal composition.

In an embodiment, a metal is added to the heel solution.

In an embodiment, the colloidal composition includes the stabilizer and a silicate doped with the metal such that the stabilizer and the metal are dispersed within one or more particles of the silicate.

In an embodiment, the metal includes about 35 wt % or less based on silica.

In an embodiment, the colloidal composition is further processed to form a crystalline structure.

In an embodiment, the colloidal composition is further processed by heating.

In an embodiment, a metal is added to the heel solution prior to crystallization.

In an embodiment, the colloidal composition includes a zeolite.

In an embodiment, the stabilizer includes a quaternary amine.

In still yet another embodiment, the present invention provides a method of forming a colloidal silicate composition. The method includes preparing a silicic acid solution, a metal silicate solution and an alkaline solution; mixing and further processing the silicic acid solution and the metal silicate solution with the alkaline solution; and forming one or more silicate particles doped with a metal wherein the metal is dispersed within one or more of the silicate particles.

In an embodiment, the metal is dispersed in a controlled manner.

In an embodiment, the silica doped with metal includes about 2 wt % or less of the metal based on silica.

In an embodiment, the metal includes an alkali metal, an alkaline earth metal, a $1^{st}$ row transition metal, a $2^{nd}$ row transition metal, a lanthanide, and combinations thereof.

In a further embodiment, a method of controlling a location of a metal within a metal-containing silica colloid is provided. The method includes preparing a silicic acid solution, a metal silicate solution and an alkaline solution; and selectively adding the metal silicate solution and the silicic acid solution to the alkaline solution to form a colloid of silica particles containing the metal.

In an embodiment, the method further comprises adding the metal silicate solution before the silicic acid solution and forming the colloid of silica particles having the metal dispersed within an interior layer of one or more of the silica particles.

In an embodiment, the method further comprises adding the silicic acid solution before the metal silicate solution and forming the colloid of silica particles having the metal dispersed within an outer layer of one or more of the silica particles.

In an embodiment, the method further comprises adding the metal silicate solution and the silicic acid solution in an alternating manner and forming the colloid of silica particles having a metal-containing layer and a non-metal containing layer.

In an embodiment, of the silica particles includes a layered structure that has the non-metal containing layer disposed on the metal containing layer in a repeat manner.

Additional features and advantages of the present invention are described in and will be apparent from the following Detailed Description of the Presently Preferred Embodiments.

DETAILED DESCRIPTION OF THE PRESENTLY PREFERRED EMBODIMENTS

The present invention generally relates to colloidal compositions and methods of preparing same. As used herein, the term "colloid" and other like terms including "colloidal", "sol", and the like refer to a two-phase system having a dispersed phase and a continuous phase. The colloids of the present invention have a solid phase dispersed or suspended in a continuous or substantially continuous liquid phase, typically an aqueous solution. Thus, the term "colloid" encompasses both phases whereas "colloidal particles" or "particles" refers to the dispersed or solid phase.

More specifically, the present invention relates to colloidal compositions that include a silicate and that can be made in a readily and cost effective manner as described below in greater detail. In general, the present invention provides two types of synthesis procedures. In one synthesis procedure, the present invention utilizes a heel solution that includes a stabilizer, such as a quaternary compound. The stabilizer can enhance the colloidal synthesis in a number of ways, such as by stabilizing and better enabling a metal to be dispersed within the silicate of the colloidal composition. It is believed that the stabilizer can also enhance the ability of the silicate to have higher metal loading, such as about 35 wt % or less based on silica. In another synthesis procedure, silicic acid and a metal silicate solution are selectively added to an alkaline solution thereby producing a colloid that includes a silicate with a metal dispersed therein in a controlled manner. The present invention is now described below in greater detail including specific examples that are illustrative of the compositions and methods of the present invention according to various embodiments without limitation.

In one embodiment of the present invention, a method of preparing a colloidal composition provides adding a silicic acid solution to a reaction vessel that includes a heel solution having an aqueous solution containing a metal component and a stabilizing component to form a colloid of silica particles. In an embodiment, the stabilizer is an amine or quaternary compound. Nonlimiting examples of amines suitable for use as the stabilizer include dipropylamine, trimethylamine, triethylmine, tri-n-propylamine, diethanolamine, monoethanolamine, triethanolamine, diisobutylamine, isopropylamine, diisopropylamine, dimethylamine, ethylenediaminetetraacetic acid, pyridine, the like and combinations thereof. Preferably, the stabilizing component is a quaternary amine that forms an alkaline solution when dispersed in water, such as quaternary ammonium hydroxides. In addition, it is further preferred that the quaternary amine includes a tetraalkyl ammonium ion wherein each alkyl group has a carbon chain length of 1 to 10, the alkyl groups being the same or different. Nonlimiting examples of quaternary amines suitable for use as the stabilizer include tetramethylammonium hydroxide (TMAOH), tetrapropylammonium hydroxide (TPAOH), tetraethylammonium hydroxide (TEAOH), tetrabutylammonium hydroxide (TBAOH), tetrahexylammonium hydroxide, tetraoctylammonium hydroxide, tributylmethylammonium hydroxide, triethylmethylammonium hydroxide, trimethylphenylammonium hydroxide, methyltripropylammonium hydroxide, dodecyltrimethylammonium hydroxide, hexadecyltrimethylammonium hydroxide, dimethyldodecylethylammonium hydroxide, diethyldimethylammonium hydroxide, the like and combinations thereof. Also, the bromide and chloride forms of the above mentioned ammonium salts can be used by passing through a hydroxide (anion)-exchange column to produce the alkylammonium hydroxide materials.

The metal can include any suitable material and be derived from any suitable material including metal salts that are soluble or substantially soluble in an aqueous solution. In an embodiment, the metal includes an alkali metal, an alkaline earth metal, a $1^{st}$ row transition metal, a $2^{nd}$ row transition metal, a lanthanide, and combinations thereof. Preferred metal components include aluminum, cerium, titanium, tin, zirconium, zinc, copper, nickel, molybdenum, iron, rhenium, vanadium, boron, the like and any combination thereof.

The silicic acid solution can be prepared by passing a sodium silicate solution through a bed of H$^+$-cation exchange resin. The resulting deionized silicic acid solution tends to be quite reactive and is typically kept cooled to retard polymerization. Upon addition of the silicic acid solution to the alkaline solution in the heel, the disassociated OH$^-$ from the stabilizer catalyzes a polymerization reaction between the cationic metal component and a silicate component from the silicic acid to form the colloid of silica particles. The reaction thereby yields a solid phase composed of the metal component, the stabilizer and silica wherein the metal and stabilizer are dispersed within the silica particles. Utilization of the stabilizer component obviates the need to provide a heel containing alkaline catalysts, such as NaOH, KOH, NH$_4$OH, the like, and combinations thereof. It should be appreciated that any suitable type of silicic acid solution can be utilized.

In addition to catalyzing particle formation, the stabilizer serves as a stabilizing agent for the metal component. Not wishing to be bound by any particular theory, it is believed that the quaternary amine cation interacts with the metal oxide anion in the heel (MO$_4^{X-}$ wherein M is the metal cation) ultimately stabilizing the metal. It is believed that the quaternary amine maintains the metal oxide anion in a four-fold coordination state or tetrahedral orientation so that silicon-to-metal ratios of four can be obtained. Stabilizing the metal component in this manner produces a greater number of silicon-metal linkages allowing the solid phase of the colloid to carry an increased amount of metal compared to surface treated colloids, for example.

In an embodiment, the resultant silica colloid is capable of supporting from about 0.0001 wt % to about 35 wt % metal based on silica. The metal-stabilized silica solid phase also demonstrates increased stability and remains stable in a pH range of about 1 to about 14. The skilled artisan will appreciate that "stable" means that the solid phase of the colloid is present, dispersed through the medium and stable throughout this entire pH range with effectively no precipitate. The solid phase in an embodiment is amorphous and has a number of particles that are generally spherical in shape. The colloidal particles have a diameter in the range of about 2 nanometers (nm) to about 1000 nm pursuant to an embodiment.

In another embodiment of the present invention, silicic acid is utilized to incorporate or disperse a metal component into the framework of colloidal silica (i.e., doping). The method includes preparing a heel. The heel includes an aqueous solution that at least includes a quaternary amine as defined herein or an alkaline agent. Suitable alkaline agents include, for example, NaOH, KOH, NH$_4$OH, the like and combination thereof. The silicic acid solution (can be prepared as previously discussed or other suitable manner) is reacted with a cationic metal component to form a metal silicate solution, represented chemically below:

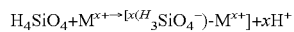

The metal silicate solution is subsequently added to the heel to form the colloid. During particle formation, the OH$^-$ present in the heel catalyzes the copolymerization of the cationic metal component and silicate (SiO$_4^-$) from the silicic acid. This produces a colloid with the metal dispersed within the silicate (i.e., incorporated into the particle framework as discussed above), such as having a homogenous distribution of the metal component throughout the entire solid phase of the colloid. Not wishing to be bound by any particular theory, it is believed that the dispersion and loading of the metal is obtained as the copolymerization forms a metal-silicate lattice throughout the microstructure of the solid phase. Nonlimiting examples of suitable metals that can be used as the cationic metal component include aluminum, cerium, titanium, tin, zirconium, zinc, copper, nickel, molybdenum, iron, rhenium, vanadium, boron, 1$^{st}$ and 2$^{nd}$ row transition metals, lanthanides, alkali metals, alkaline earth metals, the like and any combination thereof. As previously discussed, the metal component can be derived from any suitable metal source including, for example, any suitable metal salt that is soluble or substantially soluble in an aqueous solution.

According to this synthesis procedure pursuant to an embodiment, metal silicate colloids of the present invention can have a metal content from about 0.0001% to about 2% by weight based on silica. The metal silicate colloids of the present invention are amorphous and generally spherical in shape, wherein the particles have an effective diameter or particle size from about 2 nm to about 1000 nm in an embodiment. The metal silicate colloids are stable at a pH range from about 1 to about 14, exhibiting effectively no precipitation in this range. The skilled artisan will appreciate that the size of the colloidal particles can be adjusted by varying the addition time of the metal silicate solution to the heel.

As previously discussed, the above-described synthesis procedure can be utilized to effectively control the location of the method and loading thereof within the colloidal particles. In an embodiment, the metal silicate solution and the silicic acid solution are selectively added to the heel to control the position of the metal within the solid phase of the colloid as desired. Both silicic acid solution and metal silicate solution can be added to the heel to initiate particle formation or to grow or otherwise increase the size of a pure silica particle initially added to the heel. For example, the metal silicate solution is added to the heel before the silicic acid solution in an embodiment. This addition sequence yields a metal containing silica colloid wherein the metal is dispersed in a core or interior layer of the colloidal particle. The subsequent addition of the silicic acid can be used to cover the interior metal-containing portion of the particle with a layer containing on silica without the metal.

Alternatively, the silicic acid solution can be added to the heel prior to the addition of the metal silicate solution in an embodiment. This addition sequence yields colloidal particles having a core or interior composed of silica. The metal silicate solution can then be added to coat the silica particle to produce a particle containing metal on an exterior surface or outer layer of the particle wherein the metal is dispersed within this particle layer. The skilled artisan will appreciate the myriad of possibilities available for the composition of the colloid solid phase. Addition of only the metal silicate solution to the heel can yield a colloid having a dispersion or distribution of metal within one or more of the colloidal particle as previously discussed. Adding the metal silicate solution and the silicic acid solution in an alternating manner or a sequence such as metal silicate-silicic acid-metal silicate-silicic acid can yield a colloidal particle having a number of layers wherein metal containing layers are separated by layers containing silica and without a metal in an embodiment. It will be appreciated that the duration of silicic acid and/or metal silicate addition can be varied as desired to vary the width or thickness of each particle layer in the colloid. The multiple layered colloid particles of the present invention are generally spherical in shape and have an effective particle size of about 2 nm to about 1000 nm according to an embodiment.

It should be appreciated that the colloidal compositions and methods of making same can be modified in any suitable manner. For example, the colloidal compositions as described above can be further processed to form a crystalline structure, such as a crystalline silicate, a crystalline metallosilicate including a zeolite, the like and combinations thereof. In an embodiment, continued hydrothermal treatment at suitable temperatures and over a suitable period of time can produce a more crystalline silicate including metallosilicates, such as zeolites, from the colloidal compositions described-above wherein the colloidal composition includes silicate and a stabilizer with or without a metal dispersed within the silicate, specific examples of which are provided below in greater detail.

According to an embodiment, if the heel in the second synthesis procedure is replaced with an organic cation such as those used in synthesis procedure one (e.g., a stabilizer including tetramethylammonium hydroxide (TMAOH), tetrapropylammonium hydroxide (TPAOH), tetraethylammonium hydroxide (TEAOH) and/or the like), continued hydrothermal treatment after the silicic acid or metal/silicic acid containing solution has been added, can result in the formation of a more crystalline silicate or metallosilicate including a zeolite.

Doped colloidal silica is useful in multitudinous industrial applications including, for example, dental applications, protein separation, molecular sieves, nanoporous membranes, wave guides, photonic crystals, refractory applications, clarification of wine and juice, chemical mechanical planarization of semiconductor and disk drive components, catalyst supports, retention and drainage aids in papermaking, fillers, surface coatings, ceramic materials, investment casting binders, flattening agents, proppants, cosmetic formulations, particularly sunscreens, and polishing abrasives in the glass, optical and electronics and semiconductor industries. The form of silica used in a particular application depends in large part on the silica particle's size and porosity characteristics. Doped colloidal silica having the desired characteristics is readily prepared according to the method of this invention.

In an embodiment, this invention is a material for use in an industrial application comprising the colloidal composition described herein.

In an embodiment, the industrial application is selected from the group consisting of catalyst supports, retention and drainage aids in papermaking, fillers, flattening agents, proppants and polishing abrasives.

The present invention will be further understood with reference to the following illustrative examples according to various embodiments without limitation.

Synthesis Procedure One

A 5 wt % tetramethylammonium hydroxide (20-25 wt %) solution was added to a 12-gallon reactor along with 10.23 wt % of deionized (DI) water. A 0.70 wt % aluminum chlorohydrate (50 wt %) solution was added to 19.82 wt % DI water. The aluminum chlorohydrate solution was then added to the reactor at room temperature at a rate of 200 mL/min. The reactor was heated to 100° C. Then, 64.25 wt % silicic acid was added to the reactor at a ramp rate of 100-220 mL/min over 3.25 hours. As shown below, Table 1 lists the physical characteristics of the colloidal aluminosilicate made in the 12-gallon reactor after it was concentrated by ultra-filtration:

TABLE 1

| Concentrated Colloidal Aluminosilicate (12 gallon reactor) | Results |
| --- | --- |
| Solids wt % (specific gravity) | 25.30 |
| $Al_2O_3 \cdot SiO_2$ wt % (ash) | 24.72 |
| Solids wt % (removing water) "includes organic moiety" | 29.75 |
| PH | 11.02 |
| Specific Gravity | 1.1671 |
| Conductance (mhos) | 7100 |
| Particle Size (nm), Titration | 5.00 |
| wt % $Al_2O_3$ (BOS), ICP | 3.93 |

Synthesis Procedure Two

1. Preparation of the Aluminum Containing Solutions
   Monomeric Containing Aluminum Solution:
   A 0.37 M $AlCl_3.6H_2O$ solution was prepared with a pH of 2.2 and was used as prepared as further described below.
   Polyvalent Aluminum Containing Solution:
   A second solution of 0.50 M $AlCl_3.6H_2O$ was prepared. This solution was passed through an ion exchange column containing an anion exchange resin (Dowex 550A ($OH^-$)). 100 g of $AlCl_3.6H_2O$ solution was passed through 100 mL of resin. The pH of the aluminum containing solution was ca. 3.4 after being passed through the column. Aluminum chlorohydrate can also be used.
2. Preparation of the Silicic Acid:
   25.00 g of (sodium silicate) was added to 57.37 g of DI water. The solution was passed through a column containing a cation exchange resin (Dowex 650C ($H^+$)). About 40 mL of resin for 100 g of diluted sodium silicate solution was used to produce a silicic acid solution. To the silicic acid solution, a suitable amount of aluminum containing solution to produce the desired concentration (ppm) of aluminum based on silica (BOS) was added as detailed below in Table 2.
3. Preparation of the Metallosilicate Colloids:

Example 1

The silicic acid solution/monomeric aluminum solution (2.93 g of 0.37 M $AlCl_3.6H_2O$ solution) was added to a caustic heel containing 0.30 g of NaOH (50 wt %) in 14.40 g of DI water over a 5.0 hours ramp. A total of 68.57 g of silicic acid solution/aluminum solution was added.

Example 2

The silicic acid solution/polyvalent aluminum solution (3.02 g of 0.50 M $AlCl_3.6H_2O$ anion-exchanged solution) was added to a caustic heel containing 0.30 g of NaOH (50 wt %) in 14.20 g of DI water over a 5.0 hour ramp. A total of 68.57 g of silicic acid solution/aluminum solution was added.

Example 3

The silicic acid solution/polyvalent aluminum solution (3.02 g of 0.50 M $AlCl_3.6H_2O$ anion-exchanged solution) was added to a caustic heel containing 0.30 g of NaOH (50 wt %) in 14.20 g of Example 2 over a 5.0 hour ramp. A total of 68.57 g of silicic acid solution/aluminum solution was added.

Example 4

The silicic acid solution/aluminum solution (3.02 g of 0.50 M $AlCl_3.6H_2O$ anion-exchanged solution) was added to a caustic heel containing 0.30 g of NaOH (50 wt %) in 14.20 g of Example 3 over a 5.0 hour ramp. A total of 68.57 g of silicic acid solution/aluminum solution was added.

Example 5: Pilot Plant Synthesis

The silicic acid solution/aluminum solution (0.67 g of a 0.87 M solution of aluminum chlorohydrate) was added to a caustic heel containing 0.11 g NaOH (50 wt %) in 3.82 g of 20 nm silica sol in 8.18 g of DI water over a 4.75 hours ramp. The reaction was heated at 93° C. A total of 87.89 g of silicic acid solution/aluminum solution was added. The final product was cation-exchanged to remove excess sodium, large particle filtered (LPC) and pH adjusted to 6.4.

Example 6: Cerium Doped Silica Colloids

A solution of 0.50 M $Ce_2(CO_3)_3$ was prepared by adding 46 g $Ce_2(CO_3)_3$ into 100 ml DI water then adding 1N HCl until dissolved. The solution was then topped up to 200 ml with DI water.

A silicic acid solution was prepared where 200 g of (sodium silicate) was added to 1000 g of DI water. The solution was passed through a column containing a cation exchange resin (Dowex 650C ($H^+$)). About 40 mL of resin for 100 g of diluted sodium silicate solution was used.

To the silicic acid solution, an amount of the cerium containing solution was added to provide the desired concentration (ppm) of cerium based on silica (BOS) as illustrated in Table 2.

The silicic acid solution/cerium solution (6.2 ml of 0.5 M $Ce_2(CO_3)_3$ solution) was added to a caustic heel containing 5 g of KOH (45 wt %) in 200 g of DI water over a 5.0 hours ramp. A total of 1200 g of silicic acid solution/cerium solution was added to produce the cerium doped silica colloids

Example 7: Titanium Doped Silica Colloids

A titanium containing solution was prepared. In particular, a solution of 0.50 M $TiCl_4$ was prepared by slowly adding 100 ml DI water into a beaker containing 9.4 g $TiCl_4$ and 10 ml isopropyl alcohol.

The silicic acid was prepared in the same fashion as described in Example 6. To the silicic acid was added an amount of the titanium containing solution to produce the desired concentration (ppm) of titanium based on silica (BOS) as illustrated below in Table 2.

The silicic acid solution/titanium solution (12.6 ml of 0.5 M $TiCl_4$ solution) was added to a caustic heel containing 5 g of KOH (45 wt %) in 200 g of DI water over a 5.0 hours ramp. A total of 1200 g of silicic acid solution/cerium solution was added to produce the titanium doped silica colloid.

Example 8: Zinc Doped Silica Colloids

The zinc containing solution used in this procedure was a commercially-available product, namely 1N $Zn(NO_3)_2$. The silicic acid was prepared in the same fashion as described in Example 6. To the silicic acid was added an amount of zinc containing solution to provide the desired concentration (ppm) of zinc based on silica (BOS) as illustrated below in Table 2. The silicic acid solution/zinc solution (6 ml of 1 M $Zn(NO_3)_2$ solution) was added to a caustic heel containing 5 g of KOH (45 wt %) in 200 g of DI water over a 5.0 hours ramp. A total of 1200 g of acid sol/cerium solution was added to produce the zinc doped silica colloid.

Synthesis Procedure Three. Preparation of Crystalline Silicate and Metallosilicate Colloids

Example 9: Colloidal Silicalite-1 was Synthesized with a Narrow Particle Size Distribution from a Mole Composition of

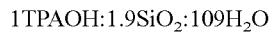

1TPAOH:1.9SiO$_2$:109H$_2$O

The source of silica was silicic acid. The reactor vessel was charged with a 20-25 wt % solution of TPAOH, which was heated to 90° C. To this, the silicic acid was added over 3 hours. A clear solution resulted, which was heated for 18 hours.

Example 10: Colloidal ZSM-5 was Synthesized with a Narrow Particle Size Distribution from a Mole Composition of

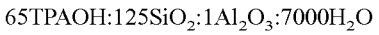

65TPAOH:125SiO$_2$:1Al$_2$O$_3$:7000H$_2$O

The source of silica was silicic acid. The reactor vessel was charged with a 20-25 wt % solution of TPAOH, which was heated to 90° C. To this the aluminum/silicic acid solution was added over 2 hours. A clear solution resulted, which was heated for 24 hours.

Metallosilicate Colloids:

Table 2 shows the various prepared metal doped samples with the different heels, pH of the different metal containing solutions, amounts of metal added to the acid sol based on silica (BOS) and a variety of characterization techniques to determine particle size and the extent, if any, agglomeration. As shown below, Table 2 provides a summary of the synthesis procedures according to Examples 1-10 as detailed above:

TABLE 2

| Sample (Heel) | Metal source and pH | Theoretical and calculated (ICP) amounts of metal BOS$^a$ (ppm) | Particle diameter QELS and (TEM) (nm) | Particle diameter (nm) and (surface area) m$^2$/g Titration | Observations | pH final solution [Final wt % metal doped SiO$_2$] |
|---|---|---|---|---|---|---|
| Example 1 (H$_2$O/NaOH) | AlCl$_3$•6H$_2$O 2.2 | 3,500 (3,281) | 47.8 (29.6) | 12.9 (233) | Prec. | 7.68 [6.54] |
| *Example 2 (H$_2$O/NaOH) | AlCl$_3$•6H$_2$O 3.4 anion-exchanged | 5,000 (1,508) | 28.5 (27.3) | 15.3 (196) | No prec. | 9.60 [6.63] |
| *Example 3 | AlCl$_3$•6H$_2$O 3.4 anion-exchanged | 5,000 (3,683) | 47.9 (51.1) | 20.9 (143) | No prec. | 9.20 [7.33] |
| *Example 4 | AlCl$_3$•6H$_2$O 3.4 anion-exchanged | 5,000 (3,911) | 82.8 (89.9) | 24.3 (123) | No prec. | 9.05 [7.67] |
| Example 5 | Al$_2$(OH)$_5$Cl•2H$_2$O 3.8 | 3,192 (2,446) | 49.3 (53.9) | 29.4 (102) | No prec. | 6.87 [32.7] |
| Example 6 | Ce$_2$(CO$_3$)$_3$ | 11650 | 50.8 | | No prec. | 5.55 |
| Example 7 | TiCl4 | 3985 | 45.7 | | No prec. | 5.42 |
| Example 8 | Zn(NO$_3$)$_2$ | 5438 | | | No prec. | 5.38 |
| Example 9 | — | — | 241 | | No prec. Silicalite by XRD | 11.5 |
| Example 10 | Al$_2$(OH)$_5$Cl•2H$_2$O 3.8 | 26000 | 292 | | No prec. ZSM-5 byXRD | 11.5 |

*Aluminum source is anion exchanged to remove chloride and increase pH.
$^a$BOS means based on silica. Example 5 after cation deionization and pH adjusted to 6.87.

In general, the metal doped colloids described above and made pursuant to various embodiments exhibit good stability in the pH range 3-9. For example, a stability test was conducted on the filtered and cation deionized aluminosilicate colloid of Example 5. The pH was adjusted to 4.1, 6.5 and 8.5 and effective particle diameters were measured (QELS) before and after heat treatment for two weeks at 60° C. No gelation occurred with these samples after heat treatment and the particle diameters remained essentially the same as demonstrated below in Table 3:

TABLE 3

| pH | Particle Diameter (Initial) (QELS, nm) | Particle Diameter (After Heating @ 60° C./two weeks) (QELS, nm) |
|---|---|---|
| 4.1 | 49.6 | 48.6 |
| 6.5 | 49.6 | 49.6 |
| 8.5 | 49.6 | 49.2 |

The colloidal compositions of the present invention can be utilized in a number of different and suitable types of applications in any suitable forms and amounts thereof. For example, the colloidal composition can be used as a chemical mechanical polishing agent including use for electronic components; a catalyst material and supports thereof including use in the petrochemical industry, such as cracking to increase fractions of gasoline; as a detergent or agent thereof to remove calcium ions and/or the like from solution; and any other types of suitable applications.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A method of producing a silica colloid, comprising:
providing an alkaline solution having a stabilizing component,
adding a silicic acid solution to the alkaline solution, and forming a colloid of silica particles, wherein the stabilizing component is dispersed throughout each silica particle,
wherein the alkaline solution comprises a cationic metal component.

2. The method of claim 1, wherein the metal component is dispersed within one or more of the silica particles.

3. The method of claim 2, wherein the stabilizing component and/or the metal component is dispersed in a homogenous manner.

4. The method of claim 1, wherein the stabilizer is a quaternary compound.

5. The method of claim 4, wherein the stabilizer is a quaternary amine.

6. The method of claim 5, wherein the quaternary amine is quaternary ammonium hydroxide.

7. A method of preparing a metal-containing silica colloid, comprising:
adding a silicic acid solution to an alkaline solution to form a mixture;
adding a metal-silicate solution to the mixture,
forming a colloid of metal silicate particles.

8. The method of claim 7, wherein the colloid is further processed to form a crystalline structure.

9. The method of claim 8, wherein the further processing comprises heating.

* * * * *

UNITED STATES PATENT AND TRADEMARK OFFICE
CERTIFICATE OF CORRECTION

PATENT NO. : 10,730,756 B2
APPLICATION NO. : 15/877168
DATED : August 4, 2020
INVENTOR(S) : Brian T. Holland et al.

Page 1 of 1

It is certified that error appears in the above-identified patent and that said Letters Patent is hereby corrected as shown below:

On the Title Page

Column 2, Item (56) (OTHER PUBLICATIONS), Line 2 - Delete "HydrodechlLorination" and insert --Hydrodechlorination--;

Column 2, Item (56) (OTHER PUBLICATIONS), Line 8 - Delete "$SiO^2$," and insert --$SiO_2$,--; and Column 2, Item (57) ABSTRACT, Line 5 - Before "dispersion" delete "and".

Signed and Sealed this
Fifteenth Day of December, 2020

Andrei Iancu
*Director of the United States Patent and Trademark Office*